US006737399B2

(12) United States Patent
Nuttall et al.

(10) Patent No.: US 6,737,399 B2
(45) Date of Patent: May 18, 2004

(54) TREATMENT OF CONJUNCTIVITIS

(75) Inventors: Patricia Anne Nuttall, Culham (GB); Guido Christiaan Paesen, Jericho (GB)

(73) Assignee: Evolutec Ltd., Oxford (GB)

( * ) Notice: Subject to any disclaimer, the term of this patent is extended or adjusted under 35 U.S.C. 154(b) by 0 days.

(21) Appl. No.: 10/085,572

(22) Filed: Feb. 27, 2002

(65) Prior Publication Data

US 2002/0151499 A1 Oct. 17, 2002

Related U.S. Application Data

(63) Continuation of application No. PCT/GB00/03282, filed on Aug. 24, 2000.

(30) Foreign Application Priority Data

Sep. 1, 1999 (GB) .............................................. 9920674

(51) Int. Cl.[7] .......................... A61K 38/00; C07K 1/00; C07K 7/00; C07K 14/435

(52) U.S. Cl. .............................. 514/2; 514/12; 530/300; 530/324; 530/325; 530/350; 530/855; 530/858

(58) Field of Search ....................... 514/2, 12; 530/300, 530/324, 325, 350, 855, 858

(56) References Cited

FOREIGN PATENT DOCUMENTS

| WO | WO 97/44451 | 11/1997 |
|----|-------------|---------|
| WO | WO 99/27104 | 6/1999  |

OTHER PUBLICATIONS

Bisca et al., Current Therapeutic Research, 58:828–841 (1997).
Chapin et al., Faseb, 14:A183.

*Primary Examiner*—Jon P. Weber
*Assistant Examiner*—Kailash C. Srivastava
(74) *Attorney, Agent, or Firm*—Klauber & Jackson

(57) ABSTRACT

The present invention relates to the discovery that various proteins isolated from ticks are effective in the treatment of conjunctivitis. These proteins may most suitably be applied topically to an affected area and are effective to ameliorate the symptoms of this condition.

8 Claims, 6 Drawing Sheets

FIG. 3
Mean Change From Baseline Redness Scores Following Pre-Treatment With Either 10% HBP Or Saline

FIG. 4

Mean Change From Baseline Chemosis Scores Following Pre-Treatment With Either 6% HBP Or Saline

TREATMENT OF CONJUNCTIVITIS

This application is a continuation of International application number PCT GB00/03282 filed Aug. 24, 2000.

The present invention relates to the discovery that various proteins isolated from ticks are effective in the treatment of conjunctivitis. These proteins may most suitably be applied topically to an affected area and are effective to ameliorate the symptoms of this condition.

Conjunctivitis, or "pink eye", is the name given to the inflammation of the conjunctiva of the eye when exposed to bacteria, viruses or other irritants. Conjunctivitis is the most common eye disease in the developed world and can vary in severity from a mild inflammation with tearing to a severe inflammation that causes tissue injury. The most common cause of conjunctivitis is viral infection, caused mainly by adenovirus. Other types of conjunctivitis include bacterial and fungal disease, caused mainly by *Haemophilus influenzae* and *Streptococcus pneumoniae*.

Non-infective, or allergic, conjunctivitis is characterised by ocular redness and itching and may involve mucus production in the eye. Other clinical manifestations are tearing (clear tears), crusting of the eyelids and photophobia. This condition is normally seasonal and is very frequent in patients that suffer from allergic rhinitis.

Conventionally, allergic conjunctivitis is treated using an ophthalmic preparation that contains a topical decongestant, either with or without an antihistamine agent. This condition may also respond to treatment for underlying allergies and may disappear when the causative allergen is removed. The occurrence of allergic conjunctivitis in susceptible individuals can also be prevented by the topical application of sodium chromoglycate. Recent developments in this field also support the usefulness of mast cell stabilising drugs in the treatment of ocular allergy.

Seasonal allergic conjunctivitis involves type-1 hypersensitivity (IgE), whilst the other main forms of ocular allergies, such as perennial allergic conjunctivitis, vernal and atopic keratoconjunctivitis and giant papillary conjunctivitis, have a more complex immunological basis and a chronic inflammatory component. In order to control the ocular inflammation caused by these types of conjunctivitis, thoughtful patient management is needed in order to avoid incurring steroid-induced side effects that result from many treatment regimes. The widespread incidence of allergic conjunctivitis means that there is a continuing need for the discovery of novel agents that are effective to ameliorate the symptoms of this condition.

Antigen activates the release of mediators of ocular allergy from the mast cells found in the eye. Histamine is one of these mediators, which is present in the secretory granules of mast cells and basophils and is formed by decarboxylation of histidine.

Histamine has been implicated in the redness and itching found in seasonal eye allergy. Anti-histamine compounds that bind to histamine receptors in the eye have been found to be useful in treating the signs and symptoms of eye allergy. Most of these drugs are compounds that are structurally related to histamine and bind to its receptor(s), thereby obstructing the interaction of histamine with its receptor(s). However, the drugs that are currently available often have undesirable side effects (for example drowsiness) and are not always effective.

Conventional $H_1$ receptor antagonists are widely used as antihistamine agents for treating allergic reactions including allergic rhinitis (hay fever), urticaria, insect bites and drug hypersensitivities. $H_1$ receptor antagonists target the redness and inflammation that is associated with these conditions. However, there are numerous undesirable effects of the $H_1$ receptor antagonists currently used. When used for purely antihistamine actions, all of the effects on the central nervous system (CNS) are unwanted. When used for their sedative or anti-emetic actions, some of the CNS effects such as dizziness, tinnitus and fatigue are unwanted. Excessive doses can cause excitation and may produce convulsions in children. The peripheral anti-muscarinic actions are always undesirable. The commonest of these is dryness of the mouth, but blurred vision, constipation and retention of urine can also occur. Unwanted effects not related to the drug's pharmaceutical action are also seen. Thus, gastrointestinal disturbances are fairly common while allergic dermatitis can follow topical application of these drugs.

$H_2$ receptor antagonists are also used as anti-histamine agents. These agents target the itching that is associated with the condition as a result of activation of certain aspects of the nervous system.

In addition to the problems mentioned above, some histamine antagonists are troublesome if taken with alcohol or with drugs. For example, the antihistamine Seldane used in combination with antibiotics and antifungals may cause the threatening side-effects It can therefore be seen that drugs used to control the actions of histamine are not always effective. The reasons why they may have limited efficacy may relate to the specificity of these drugs for only a subclass of histamine receptors, particularly when a certain class of conditions requires interference with a larger class of receptors. Indeed, it is now known that there are a large number of different chemoattractants and vasoactive substances implicated in allergic conjunctivitis, liberated not only by mast cells but also by eosinophils and other cells, that produce ocular allergy in patients with ocular allergic disorders.

There is thus a great need for agents that are effective in ameliorating the symptoms of this condition, but that do not generate the side-effects that detract from their attractiveness as therapeutic compounds. Molecules that target both $H_1$ and $H_2$ receptor-mediated effects would be particularly useful in this respect.

Molecules that are capable of binding to histamine have previously been identified in blood-feeding ectoparasites, such as ticks. For example, a salivary nitric oxide-carrying haeme protein (nitrophorin) of the triatome bug *Rhodnius prolixus* has been found to bind histamine (Ribeiro and Walker, 1994). The isolation of a family of vasoactive amine binding proteins from ticks is described in co-pending International Patent Application No. PCT/GB97/01372, which is owned by the Applicant for the present invention, the contents of which are incorporated into the present application in their entirety. These proteins bind to histamine and are closely related to one another. Some of these molecules also bind to serotonin. These molecules differ markedly from any of the $H_1$, $H_2$ or $H_3$ receptor families and appear to bind to histamine in a different manner.

It has now been found, surprisingly, that these vasoactive amine binding proteins isolated from ticks, and related proteins, are remarkably effective in the treatment of conjunctivitis.

SUMMARY OF THE INVENTION

According to the present invention there is provided the use of a histacalin protein in the manufacture of a medicament for the treatment or prevention of conjunctivitis.

The present invention also provides a method for the treatment or prevention of conjunctivitis which comprises administering to a subject an effective amount of a histacalin protein.

The term "histacalin protein" in the present application denotes:

(a) any vasoactive amine binding protein that binds specifically to a vasoactive amine with a dissociation constant of less than $10^{-7}$M and which belongs to the same protein family as the proteins MS-HBP1, FS-HBP1 and HS-BBP-2 disclosed in co-pending International Patent Application No. PCT/GB97/01372 wherein a protein is considered to belong to this protein family if the primary, mature monomer sequence of the protein has no more than 260 amino acids and at least 30 of the amino acids in the protein's complete sequence are conserved as identical residues in an alignment of that protein and the proteins MS-HBP1, FS-HBP1 and FS-HBP-2, the alignment preferably having been obtained using GCG's pileup command (Program Manual for the Wisconsin Package, 1994; gap creating penalty=3; gap extension penalty=1, scoring matrix Blosum62.cmp, pileup carried out using the endweight option);

(b) a protein from a haematophagous arthropod that binds specifically to histamine with a dissociation constant less than $10^{-7}$ M and which contains the sequence motifs D/E A W K/R (preferably DAWK, more preferably QDAWK) and Y/C E/D L/I/F W (preferably Y/C EL W);

(c) a natural biological variant, such as an allelic variant or a geographical variants, of a protein as defined in (a) or (b) above;

(d) a functional equivalent of a protein as defined in (a), (b) or (c) above that contains single or multiple amino-acid substitution(s), addition(s), insertion(s) and/or deletion(s) from the wild type protein sequence and/or substitutions of chemically-modified amino acids that do not affect the biological function of binding to its respective vasoactive amine;

(e) an active fragment of a protein as defined in (a), (b), (c) or (d) above, wherein "active fragment" denotes a truncated protein that retains the biological function of binding to its respective vasoactive amine; and (f) a fusion protein comprising a protein as defined in (a), (b), (c), (d) or (e) above fused to a peptide or other protein, such as a label, which may be, for instance, bioactive, radioactive, enzymatic or fluorescent, or an antibody.

An alignment of the proteins MS-HBP1, FS-HBP1 and FS-HBP-2 obtained using GCG's pileup command (Program Manual for the Wisconsin Package, 1994; gap creating penalty=3; gap extension penalty=1, scoring matrix Blosum62.cmp. pileup carried out using the endweight option) is shown in Table 1 below.

TABLE 1

SEQUENCE COMPARISON OF FS-HBP1 (top line), FS-HBP2 (middle line) and MS-HBP1 (bottom line). Identical residues are marked "=" below the three lines of sequence. The sequences were aligned as described above

| D | K | P | V | W | A | D | E | A | A | N | G | E | H | Q | D | A | w | K | H |
|---|---|---|---|---|---|---|---|---|---|---|---|---|---|---|---|---|---|---|---|
| N | Q | P | D | W | A | D | E | A | A | N | G | A | H | Q | D | A | W | K | S |
| N |   | P | T | W | A | N | E | A | K | L | G | S | Y | Q | D | A | W | K | S |
| = |   | = | = |   | = | = |   |   |   |   |   |   |   |   | = | = | = | = | = |

| L | Q | K | L | V | E | E | N |   | Y | D | L | I | K | A | T | Y | K | N |
|---|---|---|---|---|---|---|---|---|---|---|---|---|---|---|---|---|---|---|
| L | K | A | D | V |   | E | N | V | Y | Y | M | V | K | A | T | Y | K | N |
| L | Q | Q |   |   | D | Q | N | K | R | Y | Y | L | A | Q | A | T | Q | T | T |
| = |   |   |   |   |   | = |   |   |   |   |   |   |   | = |   | = |   |   |   |

| D | P | V | W | G | N | D | F | T | C | V | G | T | A | A | Q | N | L | N | E |
| D | P | V | W | G | N | D | F | T | C | V | G | V | M | A | N | D | V | N | E |
| D | G | V | W | G | E | E | F | T | C | V | S | V | T | A | E | K | I | G |   |
| = |   | = | = | = |   |   | = | = | = | = |   |   |   | = |   |   |   |   |   |

| D | E | K | N | V | E | A | W | F | M | F | M | N | N | A | D | T | V | Y | Q |
| D | E | K | S | I | Q | A | E | F | L | F | M | N | N | A | D | T | N | M | Q |
|   | K | K | K | L | N | A | T | I | L | Y | K | N | K | H | L | T | D | L | K |
|   | = |   |   |   |   | = |   |   |   | = |   | = |   |   |   | = |   |   |   |

| H | T | F | E | K | A | T | P | D | K | M | Y | G | Y | N | K | E | N | A | I |
| F | A | T | E | K | V | T | A | V | K | M | Y | G | Y | N | R | E | N | A | F |
| E | S | H | E | T | I | T | V | W | K | A | Y | D | Y | T | T | E | N | G | I |
|   |   |   | = |   |   | = |   |   | = |   | = |   | = |   |   | = | = |   |   |

| T | Y | Q | T | E | D | G |   |   | Q | V | L | T | D | V | L | A | F | S |
| R | Y | E | T | E | D | G |   |   | Q | V | F | T | D | V | I | A | Y | S |
| K | Y | E | T | Q |   | G | T | R | T | Q | T | F | E | D | V | F | V | F | S |
|   | = |   | = |   |   | = |   |   |   |   |   |   |   |   |   |   |   |   | = |

| D |   | D | N | C | Y | V | I | Y | A | L | G | P | D | G | S | G | A | G |
| D |   | D | N | C | D | V | I | Y | V | P | G | T | D | G | N | E | E | G |
| D | Y | K | N | C | D | V | I | F | V | P | K | E | R | G | S | D | E | G | D |
| = |   |   | = | = |   | = | = |   |   |   |   |   |   | = |   |   | = |   |   |

| Y | E | L | W | A | T |   | D |   | Y | T | D | V | P | A | S | C | L | E | K |
| Y | E | L | W | T | T |   | D |   | Y | D | N | I | P | A | N | C | L | N | K |
| Y | E | L | W | V | S | E | D | K | I | D | K | I | P |   | D | C | C |   | K |
| = | = | = | = |   | = |   | = |   |   |   |   |   | = |   |   | = |   |   | = |

| F | N |   | E | Y |   | A | A | G | L | P |   | V | R | D | V | Y | T |
| F | N |   | E | Y |   | A | V | G | R | E |   | T | R | D | V | F | T |
| F | T | M | A | Y | F | A | Q | Q | Q | E | K | T | V | R | N | V | Y | T | D |
| = |   |   |   | = |   | = |   |   |   |   |   |   |   | = |   |   | = |   |   |

| S | D | C | L | P |   |   |   |   | E |
| S | A | C | L |   |   |   |   |   | E |
| S | S | C | K | P | A | P | A | Q | N |
| = |   | = |   |   |   |   |   |   |   |

Preferably, a protein is in the same family as the above proteins if it contains more than 40, more preferably more than 50, more preferably more than 60 residues, most preferably 70 residues or more which are identical as defined in a) above when aligned with the proteins shown in Table 1.

Preferably, the histacalin protein is derived from a blood-feeding ectoparasite, such as a leech, mosquito or tick. Most preferably, the histacalin protein is derived from a tick, in particular a species of hard tick such as *R. appendiculatus, I. ricinus* and *D. reticulatus*.

The histacalin proteins described above may be used for the treatment of any conjunctivitis condition. Preferably, they are used for the treatment of non-infective conjunctivitis, more preferably allergic conjunctivitis. In particular, the term allergic conjunctivitis is meant to include seasonal and perennial conjunctivitis, as well as vernal keratoconjunctivitis, giant papillary conjunctivitis and atopic keratoconjunctivitis.

The histacalin proteins as defined in above, particularly in section (e), can be used as diagnostic tools in the evaluation of the disease state of a patient who is suspected of suffering from non-infective conjunctivitis.

Any mammalian subject is suitable for treatment by the method of the present invention. Preferably, the patient is human.

Preferably, a pharmaceutically-acceptable carrier is also used in the manufacture of the medicament according to the invention. Such a pharmaceutically-acceptable carrier is also preferably used in the method of the present invention.

Suitable pharmaceutically-acceptable carriers include carriers that do not themselves induce the production of antibodies that are harmful to the individual receiving the composition. Typically, suitable carriers are large, slowly metabolised macromolecules such as proteins, polysaccharides, polylactic acids, polyglycolic acids, polymeric amino acids, amino acid copolymers, lipid aggregates (such as oil droplets or liposomes) and inactive virus particles. Such carriers are well known to those of skill in the art.

Pharmaceutically-acceptable carriers in therapeutic compositions may also contain liquids such as water, saline, glycerol and ethanol. Additionally, auxiliary substances, such as wetting or emulsifying agents and pH buffering substances, may be present. The compositions may be prepared as injectables, either as liquid solutions or suspensions. Solid forms suitable for solution or suspension in liquid vehicles prior to injection may also be prepared. Preparations for oral administration may be formulated to allow for controlled release of the active agent.

optionally one or more conventional antihistamine agents or anti-sedative agents may also be used in the manufacture of the medicament according to the invention. Such conventional antihistamine agents or anti-sedative agents may also be used in the method of the present invention. The inclusion of these agents, allows a synergistic effect on conjunctivitis.

Sometimes conventional antihistamine agents provide unwanted side-effects, such as drowsiness. In this eventuality, it may be advantageous to further include one or more anti-sedative agents in the manufacture of the medicament and in the method. Suitable anti-sedative agents are well known to those of skill in the art.

According to another aspect of the invention, there is provided a pharmaceutical composition comprising a histacalin protein as defined above, an antihistamine agent and a pharmaceutically-acceptable carrier. Particularly suitable antihistamine agents include levocablastine, ketotifen and lodoxamide.

Treatment may be occasional, for example in the case of seasonal conjunctivitis. The patient may in these cases apply the histacalin protein or a composition containing it and, optionally the other components referred to above, only when symptoms of conjunctivitis appear, or when they are likely to appear, for example, during conditions of high atmospheric pollen content.

Patients who suffer from perennial conjunctivitis may need to apply the histacalin proteins continuously to prevent the incidence of this condition. In order to ensure the application of an effective dose of the histacalin protein, the patient may need to apply it once, twice, three times or even four times daily.

The histacalin protein may be administered topically to the affected area by eye drops, ointment or aerosol spray or systemically by oral administration, such as by capsules or cartridges, or by injection. Preferably, the histacalin protein will be applied topically. For topical administration, it should be diluted in a suitable pharmaceutical carrier such as water or saline. Preferably, physiological saline, pH 7.2, is used.

The effective dose for a given situation can be determined by routine experimentation and is within the judgement of the skilled person. For example, in order to formulate a range of dosage values, cell culture assays and animal studies can be used. The dosage of such compounds preferably lies within the dose that is therapeutically effective in 50% of the population, and that exhibits little or no toxicity at this level. For the purposes of the present invention, an effective dose will be between 0.01 $\mu$g/kg and 50 $\mu$g/kg or, more typically, between 0.05 $\mu$g/kg and 10 $\mu$g/kg of the individual to which it is administered. Preferably, for topical administration to the eye, the histacalin proteins are present in solution at between 0.1% and 20%, more preferably between 1% and 10%. A suitable unit dose may range between 0.1 $\mu$g and 1 mg, preferably between 1 $\mu$g and 200 $\mu$g, more preferably between 10 $\mu$g and 100 $\mu$g for each eye. A unit dose of 96 $\mu$g to each eye has been found effective.

Various aspects and embodiments of the present invention will now be described in more detail by way of example with reference to the accompanying drawings in which.

It will be appreciated that modification of detail may be made without departing from the scope of the invention.

EXAMPLE 1

In this study, the irritability and efficacy of various concentrations of an ophthalmic solution of a histacalin protein have been evaluated in a compound 48/80 model of mast cell degranulation in the rabbit.

Compound 48/80 is the condensation product of N-methyl-p-methoxyphenethylamine with formaldehyde, and promotes the release of allergy mediators, including histamine, from the mast cell. Due to its pro-inflammatory actions, Compound 48/80 has been used to screen new anti-allergic compounds in animals (Udell el al., Am. J. Ophthalmol., 91, (2), 226–230, 1981).

In the present study, Compound 48/80 was used to determine the efficacy of the histacalin protein FS-HBP2 as described in PCT/GB97/01372 (herein referred to by its internal designation "EV131" and in the Figures by the designation "HBP") in preventing the signs of allergic conjunctivitis.

EV131 ophthalmic solution was prepared in 1% and 6% concentrations from stock that contained approximately 2 mg EV131 and 50 microliters $dH_2O$. Physiological saline, pH 7.2, was used as the buffer to make the dilutions.

Treatment was with either saline, or with 1%, 6% or 10% EV131 using the rabbit a model. Each rabbit was topically dosed in the right eye with 40 microliters EV131 solution, and in the left eye with 40 microliters saline.

Rabbits were given a baseline gross examination for hyperaemia, chemosis, mucous discharge and lid swelling. One rabbit that showed an abnormal examination (>+1 hyperaemia and corneal changes) was excluded from the study.

Five rabbits were dosed with 1% EV131 and four rabbits were dosed with 6% EV131. Ten minutes following dosing, 25 microliters of a 7.5 mg/ml of a solution of Compound 48/80 (Sigma Chemical Co., St. Louis, Mo., USA) was topically instilled in the pre-dosed eyes.

All rabbits were examined by gross examination at 3 min, 5 min, 10 min, 20 min, 60 min, 8 hours and 24 hours following challenge with Compound 48/80. Eyes were evaluated for conjunctival injection, chemosis, tearing, mucous discharge and lid swelling.

A dose of 6% (97 $\mu$g) EV131 was found to give optimum results of consistent reduction in inflammation as measured by hyperaemia, chemosis, mucous discharge and lid swelling.

After a three week refractory period, the procedure was repeated. This time, four rabbits were dosed with 6% EV131 and five rabbits were dosed with 10% EV131.

One rabbit in the 6% HBP group had mucus in both eyes. Three rabbits in the 6% group (1 rabbit at 20, 60 and 240 minutes post-challenge and 2 rabbits at 60 minutes post-challenge) had mucus only in the placebo pre-treated eye. In the 10% treated group, 1 rabbit only had mucus in the EV131 treated eye (60 minutes and 8 hours post-challenge) and three rabbits had mucus in both eyes (60 minutes and 8 hours post-challenge). The data are displayed in FIGS. 1 to 5.

EXAMPLE 2

This work concerned a study of the effect of dosing EV131 in the rabbit eye for an extended period, before 48/80-induced inflammation was assessed.

Figure 1:
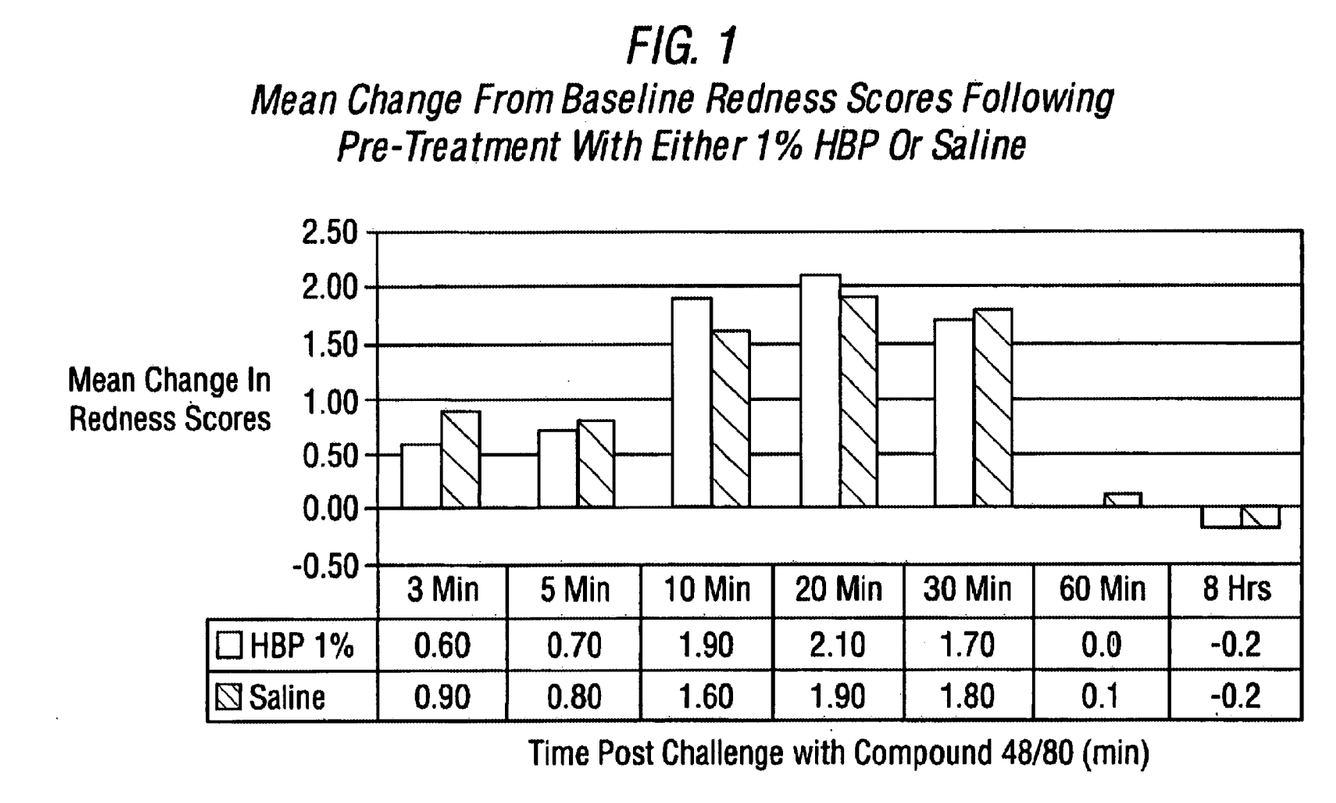
FIG. 1 shows the mean change from baseline redness scores following pre-treatment of rabbit eyes with either 1% EV131 (HBP) or saline.
Figure 2:
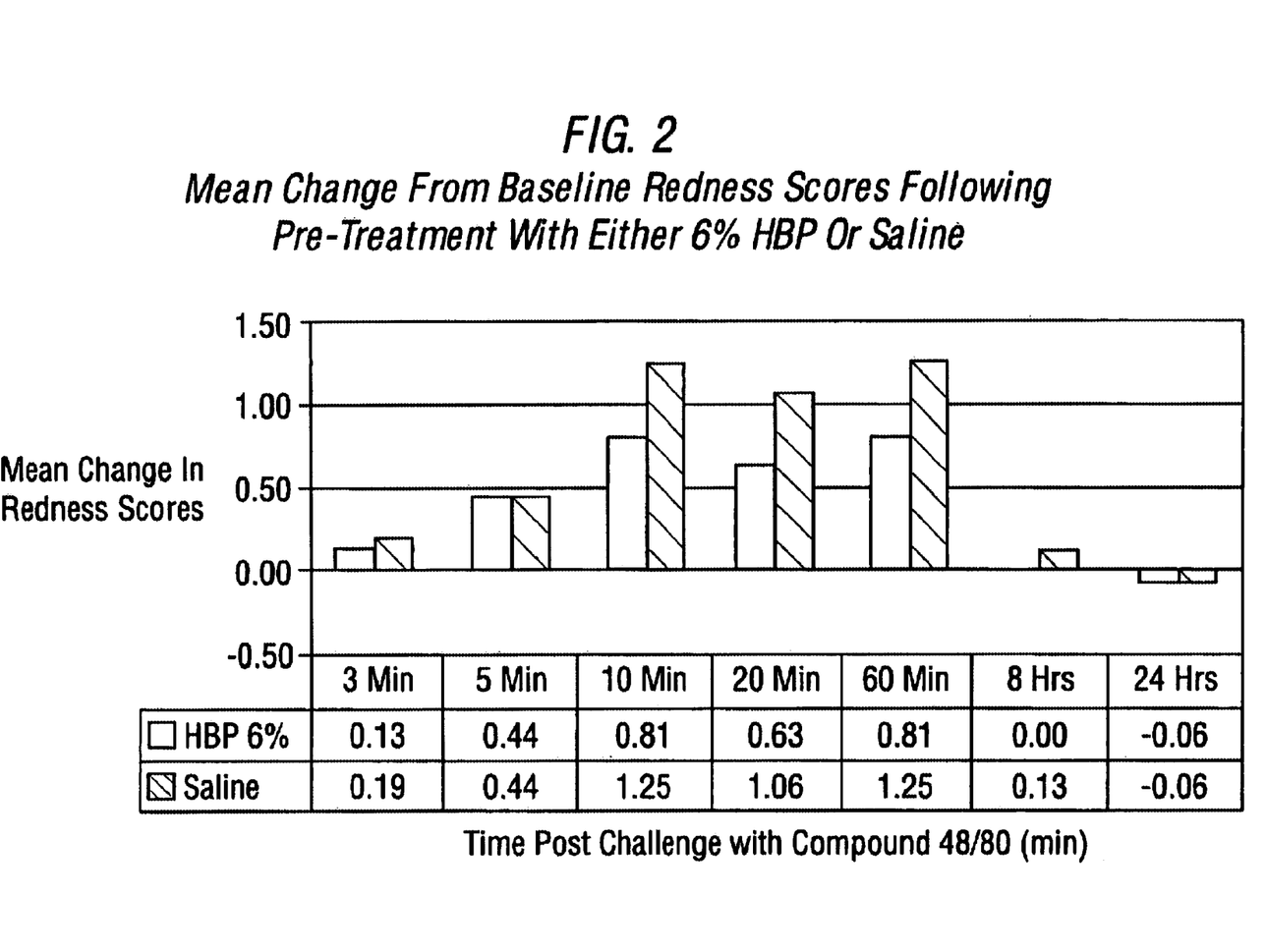
FIG. 2 shows the mean change from baseline redness scores following pre-treatment of rabbit eyes with either 6% EV131 (BP) or saline.
Figure 3:
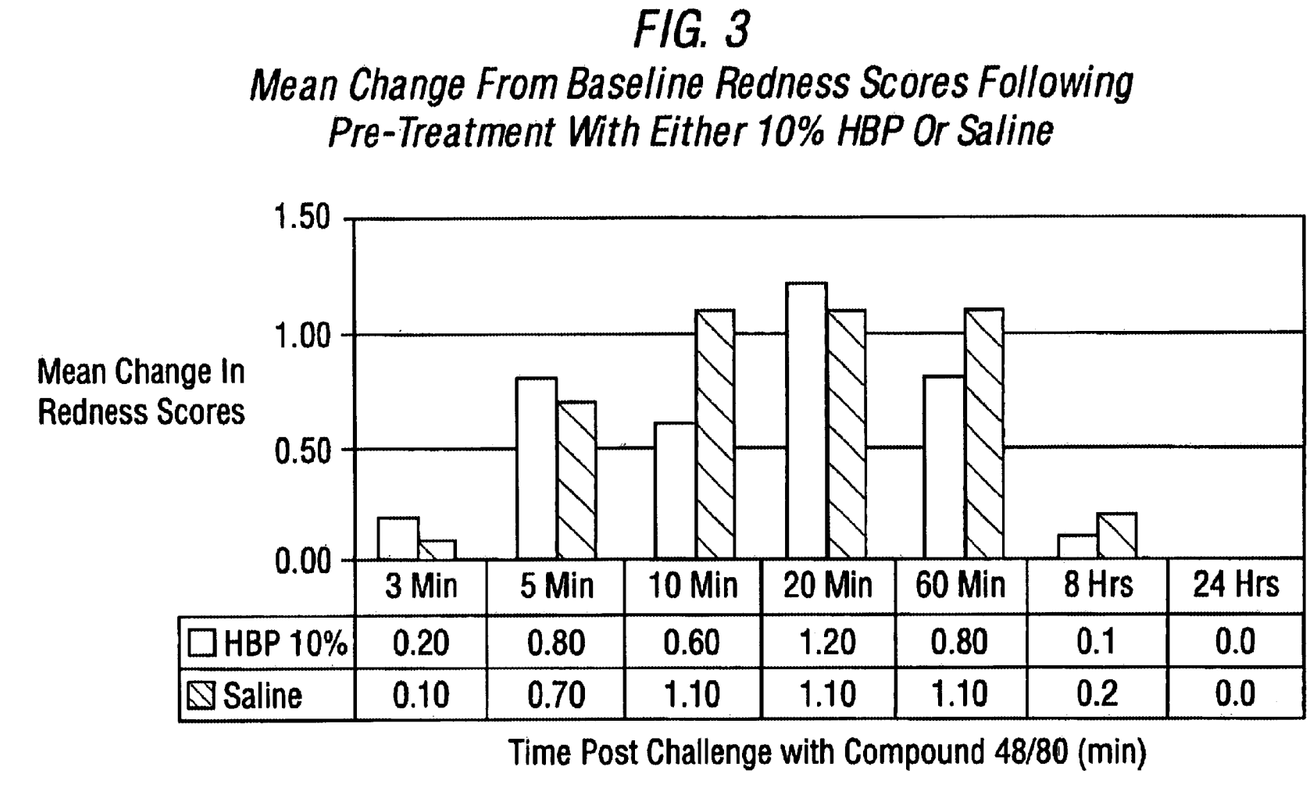
FIG. 3 shows the mean change from baseline redness scores following pre-treatment of rabbit eyes with either 10% EV131 (HBP) or saline.
Figure 4:
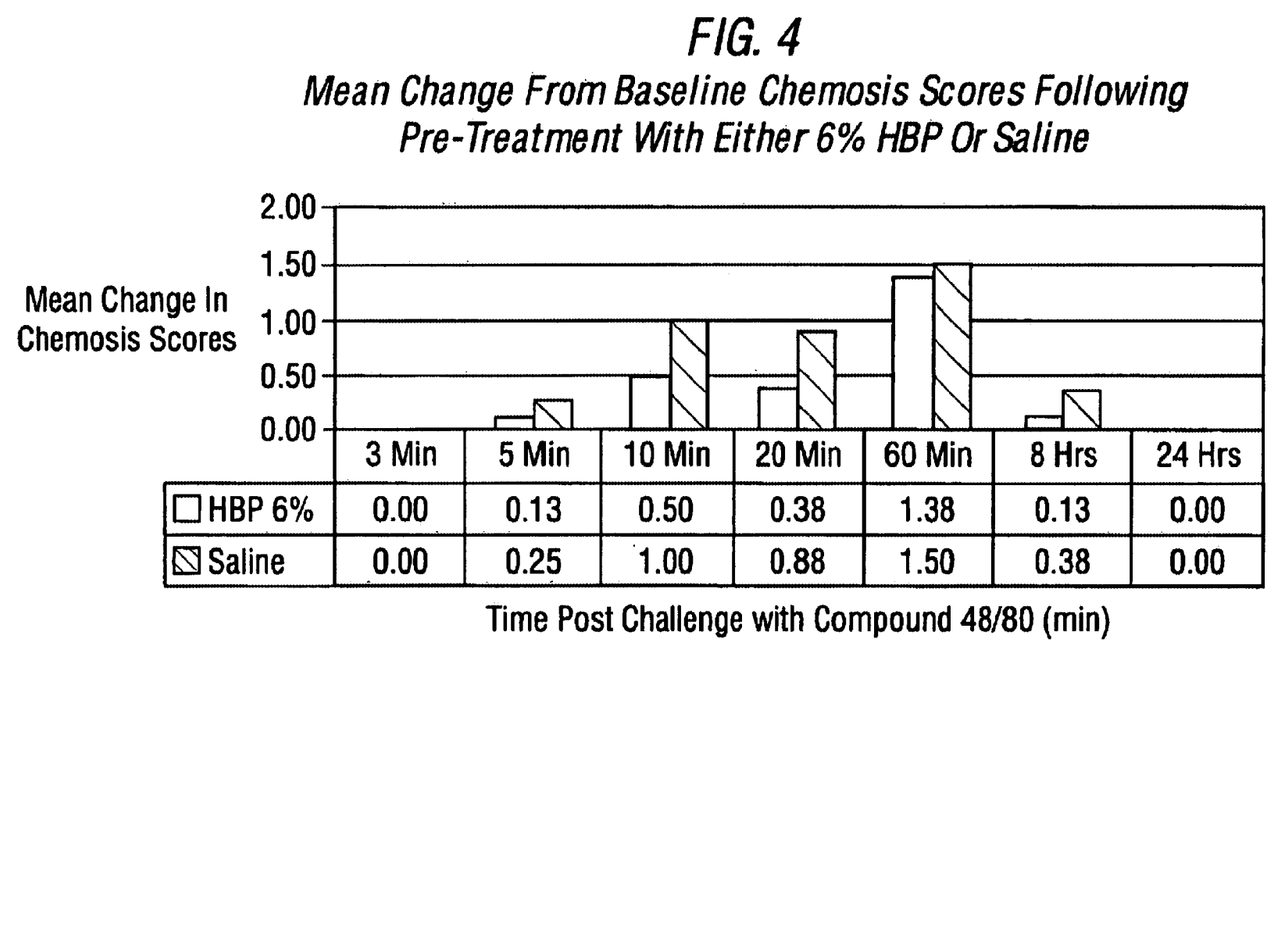
FIG. 4 shows the mean change from baseline chemosis scores following pre-treatment of rabbit eyes with either 6% EV131 (HBP) or saline.
Figure 5:
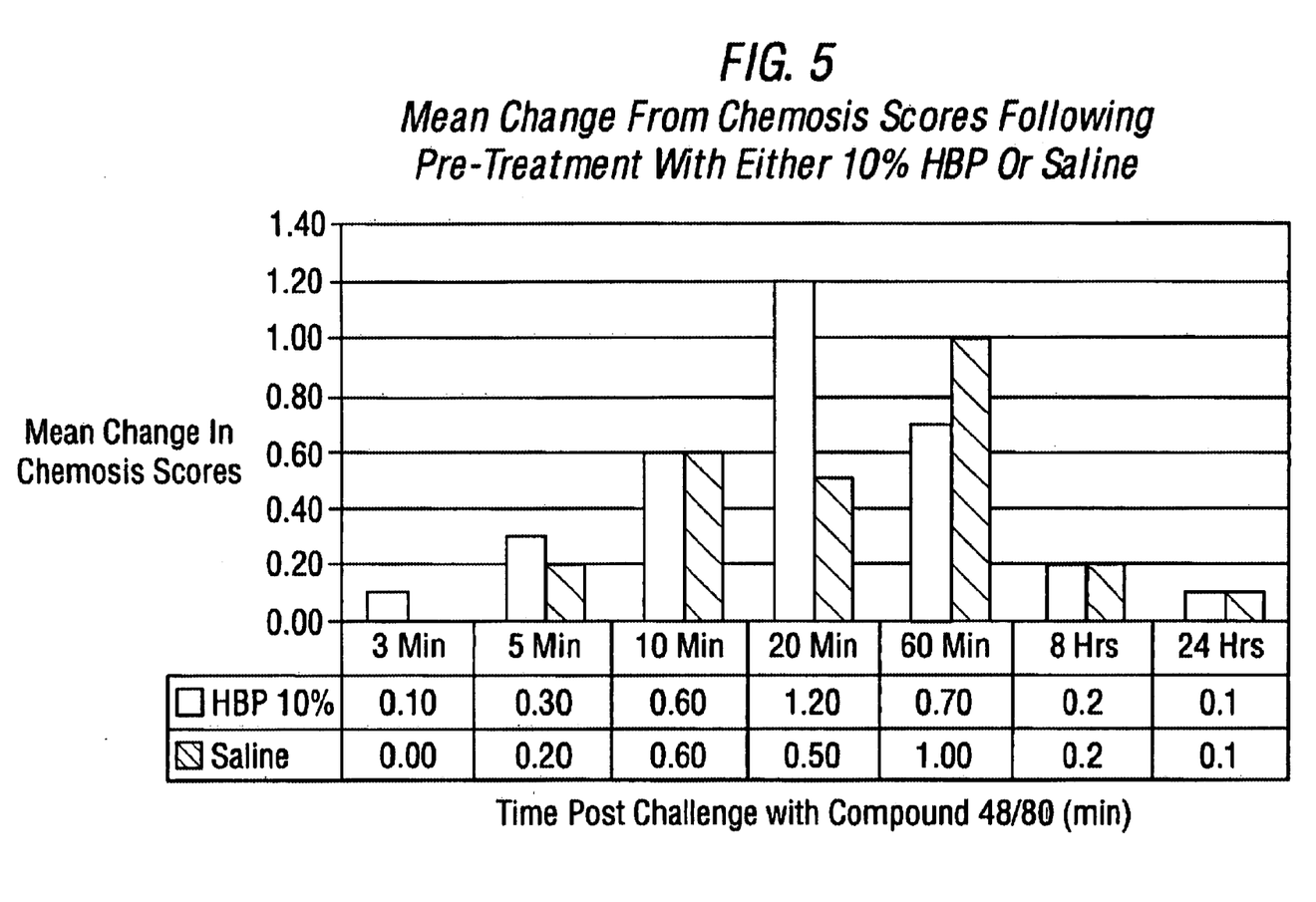
FIG. 5 shows the mean change from baseline chemosis scores following pre-treatment of rabbit eyes with either 10% EV131 (HBP) or saline.
Figure 6:
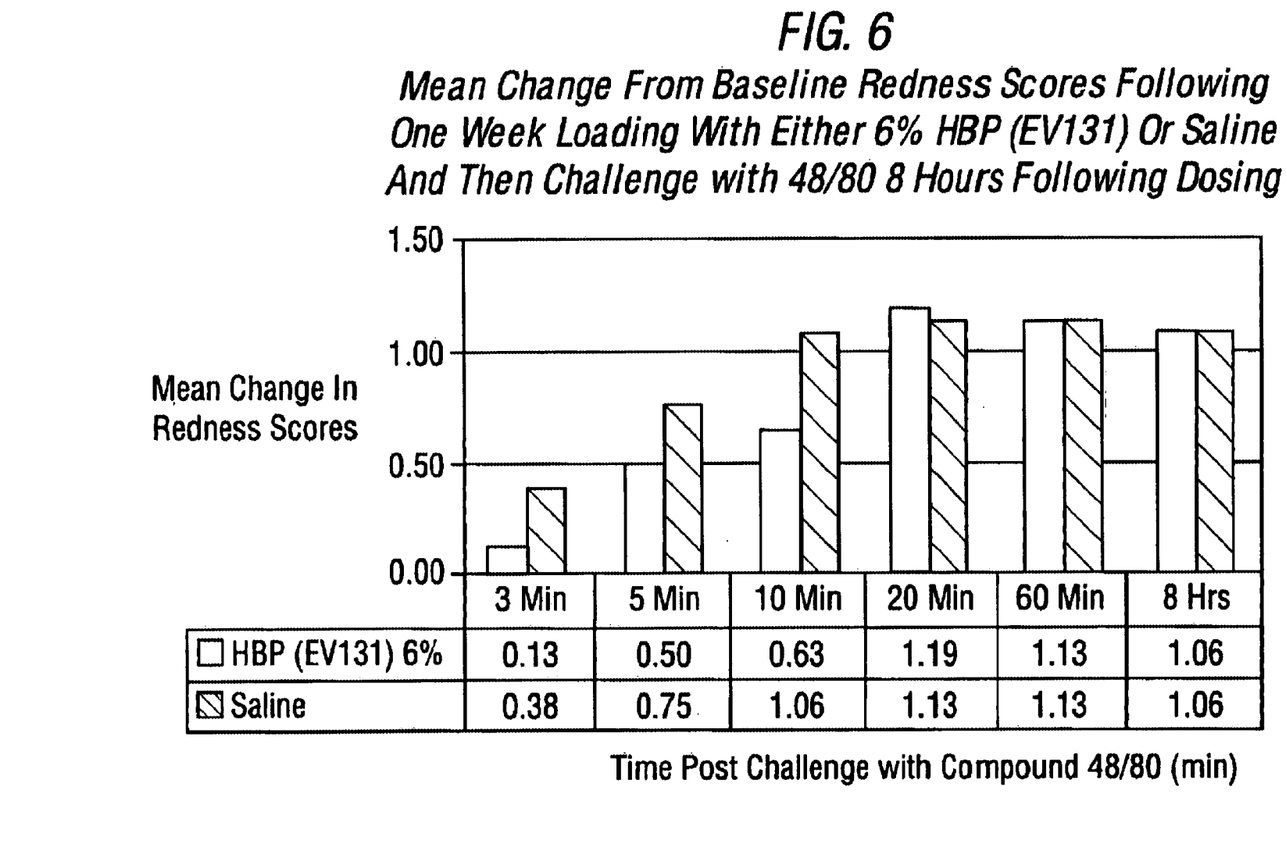
FIG. 6 shows the mean change from baseline redness scores following one week loading with either 6% EV131 or saline and then challenge with 48/80 8 hours following dosing.

Eight rabbits were used, the right eye being used for test material and the left for saline control. Each rabbit underwent a 7 day loading with EV131, 40 $\mu$l of 6% solution once daily, equivalent to a total daily dose of 96.0 $\mu$g of EV131. 40 $\mu$l of physiological saline (pH 7.2) was instilled into the left (control) eye at the same time. Eight hours following the final dose of test and control materials 25 $\mu$l of substance 48/80 (7.5 mg/ml) was instilled into each eye. Observations and scoring of eye redness were taken at 3, 10, 20 and 60 minutes and 8 hours post installation of 48/80. Mean values were calculated and are shown in FIG. 6.

The results show that at 3 minutes, there was a mean 65.0% reduction in eye redness compared to control in the EV131 eye, at 5 minutes a 33.3% reduction and at 10 minutes a 40.6% reduction. At 20 minutes there was a mean 5% increase in eye redness in the test eye compared to control. At 60 minutes and 8 hours there was no difference in eye redness between test and control eyes.

These results show that eight hours following the final dose of test and control materials, there appeared to be evidence of a protective effect of EV131 compared to saline control in reducing the degree of eye redness following instillation of substance 48/80. This effect persisted for at least 10 minutes but was not apparent at 20 minutes (i.e. 8 hours and 20 minutes following the final dose of EV131). This shows evidence of duration of action against 48/80 induced degranulation of conjunctival mast cells of at least 8 hours.

What is claimed is:

1. A method for treatment or prevention of conjunctivitis, said method comprising administering to a patient in need thereof, a medicament comprising a therapeutically effective amount of a histacalin protein.

2. A method according to claim 1, wherein said histacalin protein is a blood feeding ectoparasite histacalin protein.

3. A method according to claim 2, wherein said blood feeding ectoparasite histacalin protein is a histacalin protein.

4. A method according to claim 1, wherein said histacalin protein is an MS-HBP1, FS-HBPE1, FS-HBP2 or D.RET6 protein, a functional equivalent thereof or an active fragment thereof.

5. A method according to claim 1, wherein the medicament further comprises a pharmaceutically-acceptable carrier.

6. A method according to claim 1, wherein said conjunctivitis is non-infective conjunctivitis.

7. A method according to claim 6, wherein said non-infective conjunctivitis is allergic conjunctivitis.

8. A method according to claim 7, wherein said allergic conjunctivitis is seasonal or perennial allergic conjunctivitis.

* * * * *

SEQUENCE LISTING

<160> NUMBER OF SEQ ID NOS: 8

<210> SEQ ID NO 1
<211> LENGTH: 4
<212> TYPE: PRT
<213> ORGANISM: arthropod
<220> FEATURE:
<221> NAME/KEY: VARIANT
<222> LOCATION: 1
<223> OTHER INFORMATION: Xaa = Asp
<221> NAME/KEY: VARIANT
<222> LOCATION: 1
<223> OTHER INFORMATION: Xaa= Glu
<221> NAME/KEY: VARIANT
<222> LOCATION: 4
<223> OTHER INFORMATION: Xaa= Lys
<221> NAME/KEY: VARIANT
<222> LOCATION: 4
<223> OTHER INFORMATION: Xaa= Arg

```
<400> SEQUENCE: 1

Xaa Ala Trp Xaa
 1

<210> SEQ ID NO 2
<211> LENGTH: 4
<212> TYPE: PRT
<213> ORGANISM: arthropod

<400> SEQUENCE: 2

Asp Ala Trp Lys
 1

<210> SEQ ID NO 3
<211> LENGTH: 5
<212> TYPE: PRT
<213> ORGANISM: arthropod

<400> SEQUENCE: 3

Gln Asp Ala Trp Lys
 1               5

<210> SEQ ID NO 4
<211> LENGTH: 4
<212> TYPE: PRT
<213> ORGANISM: arthropod
<220> FEATURE:
<221> NAME/KEY: VARIANT
<222> LOCATION: 1
<223> OTHER INFORMATION: Xaa = Tyr
<221> NAME/KEY: VARIANT
<222> LOCATION: 1
<223> OTHER INFORMATION: Xaa= Cys
<221> NAME/KEY: VARIANT
<222> LOCATION: 2
<223> OTHER INFORMATION: Xaa= Glu
<221> NAME/KEY: VARIANT
<222> LOCATION: 2
<223> OTHER INFORMATION: Xaa= Asp
<221> NAME/KEY: VARIANT
<222> LOCATION: 3
<223> OTHER INFORMATION: Xaa= Leu
<221> NAME/KEY: VARIANT
<222> LOCATION: 3
<223> OTHER INFORMATION: Xaa= Ile
<221> NAME/KEY: VARIANT
<222> LOCATION: 3
<223> OTHER INFORMATION: Xaa= Phe

<400> SEQUENCE: 4

Xaa Xaa Xaa Trp
 1

<210> SEQ ID NO 5
<211> LENGTH: 4
<212> TYPE: PRT
<213> ORGANISM: arthropod
<220> FEATURE:
<221> NAME/KEY: VARIANT
<222> LOCATION: 1
<223> OTHER INFORMATION: Xaa = Tyr
<221> NAME/KEY: VARIANT
<222> LOCATION: 1
<223> OTHER INFORMATION: Xaa= Cys

<400> SEQUENCE: 5

Xaa Glu Leu Trp
 1
```

```
<210> SEQ ID NO 6
<211> LENGTH: 172
<212> TYPE: PRT
<213> ORGANISM: FS-HBP1

<400> SEQUENCE: 6

Asp Lys Pro Val Trp Ala Asp Glu Ala Ala Asn Gly Glu His Gln Asp
  1               5                  10                  15

Ala Trp Lys His Leu Gln Lys Leu Val Glu Glu Asn Tyr Asp Leu Ile
             20                  25                  30

Lys Ala Thr Tyr Lys Asn Asp Pro Val Trp Gly Asn Asp Phe Thr Cys
         35                  40                  45

Val Gly Thr Ala Ala Gln Asn Leu Asn Glu Asp Glu Lys Asn Val Glu
     50                  55                  60

Ala Trp Phe Met Phe Met Asn Asn Ala Asp Thr Val Tyr Gln His Thr
 65                  70                  75                  80

Phe Glu Lys Ala Thr Pro Asp Lys Met Tyr Gly Tyr Asn Lys Glu Asn
                 85                  90                  95

Ala Ile Thr Tyr Gln Thr Glu Asp Gly Gln Val Leu Thr Asp Val Leu
            100                 105                 110

Ala Phe Ser Asp Asp Asn Cys Tyr Val Ile Tyr Ala Leu Gly Pro Asp
            115                 120                 125

Gly Ser Gly Ala Gly Tyr Glu Leu Trp Ala Thr Asp Tyr Thr Asp Val
        130                 135                 140

Pro Ala Ser Cys Leu Glu Lys Phe Asn Glu Tyr Ala Ala Gly Leu Pro
145                 150                 155                 160

Val Arg Asp Val Tyr Thr Ser Asp Cys Leu Pro Glu
                165                 170

<210> SEQ ID NO 7
<211> LENGTH: 171
<212> TYPE: PRT
<213> ORGANISM: FS-HBP 2

<400> SEQUENCE: 7

Asn Gln Pro Asp Trp Ala Asp Glu Ala Ala Asn Gly Ala His Gln Asp
  1               5                  10                  15

Ala Trp Lys Ser Leu Lys Ala Asp Val Glu Asn Val Tyr Tyr Met Val
             20                  25                  30

Lys Ala Thr Tyr Lys Asn Asp Pro Val Trp Gly Asn Asp Phe Thr Cys
         35                  40                  45

Val Gly Val Met Ala Asn Asp Val Asn Glu Asp Glu Lys Ser Ile Gln
     50                  55                  60

Ala Glu Phe Leu Phe Met Asn Asn Ala Asp Thr Asn Met Gln Phe Ala
 65                  70                  75                  80

Thr Glu Lys Val Thr Ala Val Lys Met Tyr Gly Tyr Asn Arg Glu Asn
                 85                  90                  95

Ala Phe Arg Tyr Glu Thr Glu Asp Gly Gln Val Phe Thr Asp Val Ile
            100                 105                 110

Ala Tyr Ser Asp Asp Asn Cys Asp Val Ile Tyr Val Pro Gly Thr Asp
            115                 120                 125

Gly Asn Glu Glu Gly Tyr Glu Leu Trp Thr Thr Asp Tyr Asp Asn Ile
        130                 135                 140

Pro Ala Asn Cys Leu Asn Lys Phe Asn Glu Tyr Ala Val Gly Arg Glu
145                 150                 155                 160
```

```
Thr Arg Asp Val Phe Thr Ser Ala Cys Leu Glu
                165                 170
```

<210> SEQ ID NO 8
<211> LENGTH: 182
<212> TYPE: PRT
<213> ORGANISM: MS-HBP 1

<400> SEQUENCE: 8

```
Asn Pro Thr Trp Ala Asn Glu Ala Lys Leu Gly Ser Tyr Gln Asp Ala
 1               5                  10                  15

Trp Lys Ser Leu Gln Gln Asp Gln Asn Lys Arg Tyr Tyr Leu Ala Gln
                20                  25                  30

Ala Thr Gln Thr Thr Asp Gly Val Trp Gly Glu Glu Phe Thr Cys Val
                35                  40                  45

Ser Val Thr Ala Glu Lys Ile Gly Lys Lys Leu Asn Ala Thr Ile
                50                  55                  60

Leu Tyr Lys Asn Lys His Leu Thr Asp Leu Lys Glu Ser His Glu Thr
65                  70                  75                  80

Ile Thr Val Trp Lys Ala Tyr Asp Tyr Thr Thr Glu Asn Gly Ile Lys
                85                  90                  95

Tyr Glu Thr Gln Gly Thr Arg Thr Gln Thr Phe Glu Asp Val Phe Val
                100                 105                 110

Phe Ser Asp Tyr Lys Asn Cys Asp Val Ile Phe Val Pro Lys Glu Arg
                115                 120                 125

Gly Ser Asp Glu Gly Asp Tyr Glu Leu Trp Val Ser Glu Asp Lys Ile
                130                 135                 140

Asp Lys Ile Pro Asp Cys Cys Lys Phe Thr Met Ala Tyr Phe Ala Gln
145                 150                 155                 160

Gln Gln Glu Lys Thr Val Arg Asn Val Tyr Thr Asp Ser Ser Cys Lys
                165                 170                 175

Pro Ala Pro Ala Gln Asn
                180
```